US008078249B2

(12) United States Patent
Furnary et al.

(10) Patent No.: US 8,078,249 B2
(45) Date of Patent: *Dec. 13, 2011

(54) METHOD AND APPARATUS FOR MONITORING BLOOD CONDITION AND CARDIOPULMONARY FUNCTION

(75) Inventors: Anthony P. Furnary, Portland, OR (US); Robert I. Lowe, Portland, OR (US)

(73) Assignee: Sensicor, LLC, Portland, OR (US)

( * ) Notice: Subject to any disclaimer, the term of this patent is extended or adjusted under 35 U.S.C. 154(b) by 1627 days.

This patent is subject to a terminal disclaimer.

(21) Appl. No.: 11/367,469

(22) Filed: Mar. 3, 2006

(65) Prior Publication Data

US 2006/0149145 A1 Jul. 6, 2006

Related U.S. Application Data

(62) Division of application No. 10/280,970, filed on Oct. 24, 2002, now Pat. No. 7,010,337.

(51) Int. Cl.
*A61B 5/1455* (2006.01)
(52) U.S. Cl. ........................................ 600/325; 600/341
(58) Field of Classification Search .................. 600/310, 600/316, 322, 323, 341, 344
See application file for complete search history.

(56) References Cited

U.S. PATENT DOCUMENTS

| | | |
|---|---|---|
| 3,769,974 A | 11/1973 | Smart et al. |
| 3,878,849 A | 4/1975 | Muller et al. |
| 4,100,309 A | 7/1978 | Micklus et al. |
| 4,399,820 A | 8/1983 | Wirtzfeld et al. |
| 4,407,294 A | 10/1983 | Vilkomerson |
| 4,408,612 A | 10/1983 | Utsugi |
| 4,428,379 A | 1/1984 | Robbins et al. |
| 4,431,006 A | 2/1984 | Trimmer et al. |
| 4,671,295 A | 6/1987 | Abrams et al. |
| 4,722,347 A | 2/1988 | Abrams et al. |
| 4,815,469 A | 3/1989 | Cohen et al. |
| 4,867,141 A | 9/1989 | Nakada et al. |
| 4,886,059 A | 12/1989 | Weber |
| 4,947,854 A | 8/1990 | Rabinovitz et al. |
| 5,048,524 A | 9/1991 | Bailey |
| 5,095,910 A | 3/1992 | Powers |
| 5,127,407 A | 7/1992 | Tan |
| 5,205,292 A | 4/1993 | Czar et al. |
| 5,228,440 A | 7/1993 | Chung et al. |
| 5,265,612 A | 11/1993 | Sarvazyan et al. |
| 5,284,146 A | 2/1994 | Czar et al. |
| 5,291,896 A | 3/1994 | Fonger et al. |
| 5,304,214 A | 4/1994 | DeFord et al. |
| 5,305,745 A | 4/1994 | Zacouto |
| 5,315,995 A | 5/1994 | Rivers |
| 5,316,001 A | 5/1994 | Ferek-Petric et al. |
| 5,331,947 A | 7/1994 | Shturman |

(Continued)

FOREIGN PATENT DOCUMENTS

GB 2268074 1/1994

(Continued)

*Primary Examiner* — Eric Winakur
(74) *Attorney, Agent, or Firm* — Chernoff, Vilhauer, McClung & Stenzel, LLP

(57) ABSTRACT

Sensors located on a sensor carrier are placed adjacent one or more of a surgical patient's major thoracic blood-containing structures such as the aorta or pulmonary artery, and characteristics of blood in the blood-containing structures are determined noninvasively by measuring transmission or reflection of light or other types of energy by the blood. Emitters and receptors included in the sensors are connected electrically with suitable electronic signal generating and processing components in a package remote from the sensor carrier.

65 Claims, 10 Drawing Sheets

U.S. PATENT DOCUMENTS

| | | | |
|---|---|---|---|
| 5,335,663 A | 8/1994 | Oakley et al. |
| 5,350,419 A | 9/1994 | Bendel et al. |
| 5,363,853 A | 11/1994 | Lieber et al. |
| 5,402,777 A | 4/1995 | Warring et al. |
| 5,443,445 A | 8/1995 | Peters et al. |
| 5,507,295 A | 4/1996 | Skidmore |
| 5,531,714 A | 7/1996 | Dahn et al. |
| 5,596,988 A | 1/1997 | Markle et al. |
| 5,673,694 A | 10/1997 | Rivers |
| 5,687,719 A | 11/1997 | Sato et al. |
| 5,690,104 A | 11/1997 | Kanemoto et al. |
| 5,743,260 A | 4/1998 | Chung et al. |
| 5,743,261 A | 4/1998 | Mainiero et al. |
| 5,775,328 A | 7/1998 | Lowe et al. |
| 5,776,060 A | 7/1998 | Smith et al. |
| 5,904,708 A | 5/1999 | Goedeke |
| 5,928,155 A | 7/1999 | Eggers et al. |
| 5,941,251 A | 8/1999 | Panescu et al. |
| 5,995,860 A | 11/1999 | Sun et al. |
| 6,024,704 A | 2/2000 | Meador et al. |
| 6,070,093 A | 5/2000 | Oosta et al. |
| 6,106,475 A | 8/2000 | Lowe et al. |
| 6,106,477 A | 8/2000 | Miesel et al. |
| 6,122,536 A | 9/2000 | Sun et al. |
| 6,125,291 A | 9/2000 | Miesel et al. |
| 6,134,459 A | 10/2000 | Roberts et al. |
| 6,144,866 A | 11/2000 | Miesel et al. |
| 6,152,876 A | 11/2000 | Robinson et al. |
| 6,155,267 A | 12/2000 | Nelson |
| 6,162,180 A | 12/2000 | Miesel et al. |
| 6,198,952 B1 | 3/2001 | Miesel |
| 6,206,874 B1 | 3/2001 | Ubby et al. |
| 6,231,514 B1 | 5/2001 | Lowe et al. |
| 6,234,973 B1 | 5/2001 | Meador et al. |
| 6,277,078 B1 | 8/2001 | Porat et al. |
| 6,309,350 B1 | 10/2001 | VanTassel et al. |
| 6,716,176 B1 | 4/2004 | Weston et al. |
| 7,010,337 B2 | 3/2006 | Furnary et al. |
| 2003/0199956 A1 | 10/2003 | Struble et al. |
| 2003/0216620 A1 | 11/2003 | Jain et al. |

FOREIGN PATENT DOCUMENTS

| | | |
|---|---|---|
| WO | WO 93/03668 | 3/1993 |
| WO | WO 97/49337 | 12/1997 |
| WO | WO 99/48424 | 9/1999 |

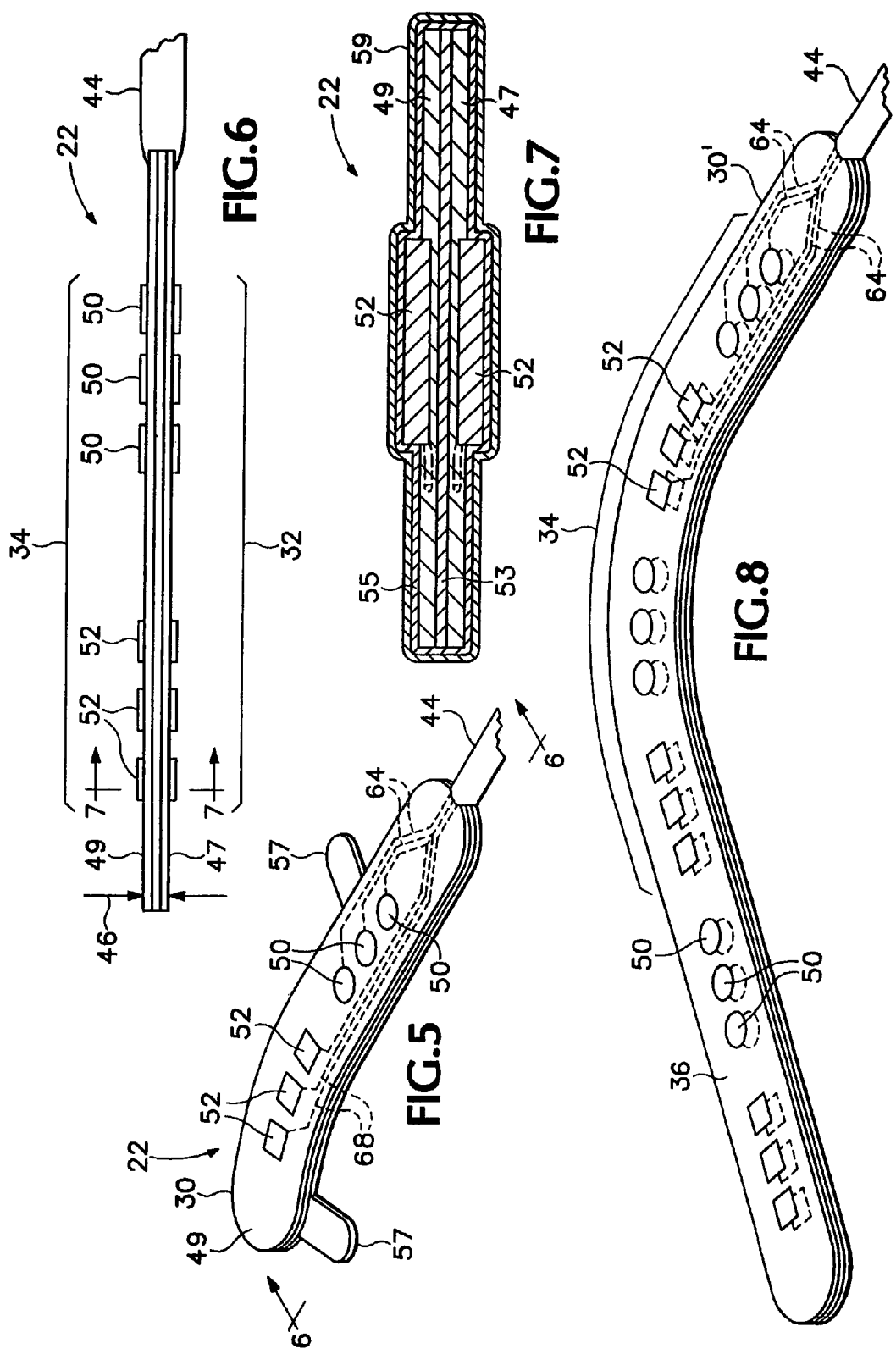

METHOD AND APPARATUS FOR MONITORING BLOOD CONDITION AND CARDIOPULMONARY FUNCTION

CROSS-REFERENCE TO RELATED APPLICATIONS

This application is a division of U.S. patent application Ser. No. 10/280,970 filed Oct. 24, 2002, now U.S. Pat. No. 7,010,337.

BACKGROUND OF THE INVENTION

The present invention relates to monitoring a patient's cardiopulmonary function and blood condition, and particularly to a method and apparatus for monitoring the performance of a patient's heart and lungs during and following thoracic surgery.

Cardiac output means the volume rate at which the heart pumps blood. The cardiac output is important to a clinician as an indication of how well a person's heart is able to function. Using conventional techniques and available apparatus it is difficult and costly to evaluate a patient's cardiac output and respiratory efficiency, and the process cannot be performed as quickly as desirable. Following surgery, and particularly heart surgery, it would be advantageous to be able to determine quickly and frequently how well a patient's heart and lungs are performing in delivering oxygenated blood to the patient's tissues in relation to how quickly the same tissues are removing the oxygen with which they are being supplied.

To accurately determine the efficiency of the heart and lungs relative to the body's need for oxygen it is advantageous to analyze the percentage of oxygen saturation of hemoglobin (hereinafter simply called oxygen saturation) in mixed venous blood, as found in the pulmonary artery. It is also advantageous, and even more accurate in assessing a person's cardiac function, to compare the oxygen saturation of blood in the pulmonary artery with oxygen saturation in freshly oxygenated blood, as found in the aorta. In the past it has been necessary to chemically analyze drawn samples of blood to evaluate blood oxygen saturation levels accurately. Such analysis is costly, and it has usually not been practical to obtain such blood samples.

It is known to approximately evaluate the percentage of saturation of hemoglobin by oxygen (oxygen saturation) of the blood in peripheral tissues by use of an external sensor involving a light source and a receptor and evaluating the blood's effect on transmission of light through tissues immediately below the skin of an external part of a patient's body, such as the ear lobe, nose or finger. Such external sensors, known as oximeters, are available, for example, from Nellcor of Pleasanton, Calif. A measurement obtained using such a device can be used to evaluate major changes in arterial blood oxygenation, but does not provide enough information for determining a patient's cardiac output, since it does not provide enough information regarding oxygen extraction or utilization by tissues and thus is not a good enough tool for valid evaluation of a patient's cardiopulmonary function during and after cardiac surgery.

Catheters equipped with light-emitting and receiving sensors can be placed within the blood flowing through the pulmonary artery itself. Such sensors, when thus residing in the bloodstream, can be used to measure oxygen saturation in mixed venous blood. This is a relatively invasive procedure, however, and can be used for only a limited time, after which the sensors would become covered with protein deposits from the blood and would thereby lose their sensitivity.

There is no currently available implantable device that remains separate from and outside the flow of blood for measuring oxygen saturation in blood without blood samples having to be drawn for analysis.

What is desired, then, is to be able to measure various blood characteristics, such as to analyze the level of blood oxygen saturation and the levels or concentrations of other blood components, including potassium, lactate, glucose, pH, hemoglobin or hematocrit (red blood cell volume percentage), to be able to determine those aspects of blood condition rapidly and repeatedly during and following a surgical procedure and for a period of time thereafter, and to do so at a cost which is less than the cost for repeatedly drawing and chemically analyzing or microscopically examining blood samples. Additionally, it is desirable to be able to monitor such blood characteristics over a long term in some persons.

SUMMARY OF THE INVENTION

According to the present invention, electronically operated sensors are utilized to determine or evaluate certain characteristics of blood in certain major thoracic blood-containing structures, including particularly the pulmonary artery or the aorta of a mammal, particularly a human patient, and to obtain the desired information regarding those blood characteristics substantially instantaneously, without having to withdraw blood from the patient's body to analyze it. By measuring a characteristic such as oxygen saturation of hemoglobin of blood in certain blood vessels or portions of the heart the patient's pulmonary function can be evaluated. By measuring the level of oxygen saturation of the hemoglobin in mixed venous blood such as is found in the pulmonary artery, a reasonable estimate of cardiac function can be deduced.

By comparing the level of oxygen saturation of the hemoglobin in the mixed venous blood, such as is found in the pulmonary arteries, or in non mixed venous blood such as is found in the superior or inferior vena cava, with the level of oxygen saturation in recently oxygenated blood, as may be found in the aorta or the left atrium, the efficiency of a patient's heart and lungs relative to the body's extraction of oxygen from the blood can be evaluated quickly and easily, so that a clinician can determine what, if any, intervention may be necessary for improvement of the patient's condition.

In addition, such an evaluation of the patient's condition on a repeated basis during and immediately after cardiac surgery can inform health care personnel whether a patient is satisfactorily enduring a surgical procedure and whether the patient's heart, lungs and other organs are performing as expected during recovery from surgery. Similarly, such repeated evaluation can inform health care experts as to whether devices such as an artificial heart or a ventricular assist device is providing the body with enough oxygenated blood. Such repeated evaluations could be used to signal such a support device, or a cardiac pacemaker, to increase or decrease its rate of operation in order to accommodate the variations in oxygen requirements of the body during exercise as compared with rest. By measuring and comparing the level of oxygen saturation of the hemoglobin of the blood in various parts of the heart or in various other blood vessels near the base of the heart various imperfections such as an inefficient part of lung, or an abnormal non-physiologic leak or "shunt" between the chambers of the heart, may be detected and surgical repair thereof may be evaluated.

In accordance with one aspect of the present invention, a sensor carrier is utilized to hold one or more sensors respectively adjacent the heart or one of the major blood vessels such as the pulmonary artery, the aorta or the vena cava, preferably at the location where the pulmonary artery and the aorta are located closely alongside each other above the heart. The sensors may be located on opposite faces of a ribbon-like sensor carrier placed between the aorta and the pulmonary artery and alongside the respective blood vessel.

A related aspect of the present invention is the surgical provision of a space to receive sensors between the aorta and the pulmonary artery by making an appropriate incision through the connective tissue between those blood vessels and, optionally, extending along the right branch of the pulmonary artery toward the posterior side of the superior vena cava. One preferred sensor includes a remotely controlled and electrically powered light emitter, an electronic light receptor and associated electronic circuitry for evaluating the light that originated from that light emitter after the light has passed through the patient's blood. By using the receptor to measure the remaining light received after emission of known intensities and wavelengths of light and passage of that light through the wall of a blood vessel and through the blood within the blood vessel, the quantity of certain elements and compounds as constituents of the blood can be determined by comparison of the measurement of received light with known data. This can be accomplished instantaneously by the use of appropriately programmed electronic computers, which are necessary to but whose details are not an integral part of the present invention.

In addition to or instead of visible light, various forms of energy such as ultrasound, electromagnetic radiation at various radio frequencies, and light of wavelengths outside the visible spectrum, may be used by an appropriate sensor to evaluate one or more qualities of a patient's blood.

Although such sensors for analyzing the blood may be utilized separately and temporarily placed or permanently implanted, they may also be associated with and used advantageously in connection with other devices, such as heart pacing leads, ventricular assist devices, implanted artificial hearts, and chest drains.

The foregoing and other objectives, features, and advantages of the invention will be more readily understood upon consideration of the following detailed description of the invention taken in conjunction with the accompanying drawings.

BRIEF DESCRIPTION OF THE SEVERAL VIEWS OF THE DRAWINGS

FIG. 5 is a perspective view of the sensor carrier shown in FIGS. 2, 3 and 4.

FIG. 6 is a view of the sensor carrier shown in FIG. 5 taken in the direction indicated by line 6-6 in FIG. 5.

FIG. 7 is a sectional view of the sensor carrier shown in FIGS. 2-6, taken on line 7-7 of FIG. 6.

FIG. 8 is a perspective view similar to FIG. 5, showing a sensor carrier that is an alternative embodiment of the apparatus according to the invention.

DETAILED DESCRIPTION OF THE PREFERRED EMBODIMENTS

Figure 1:
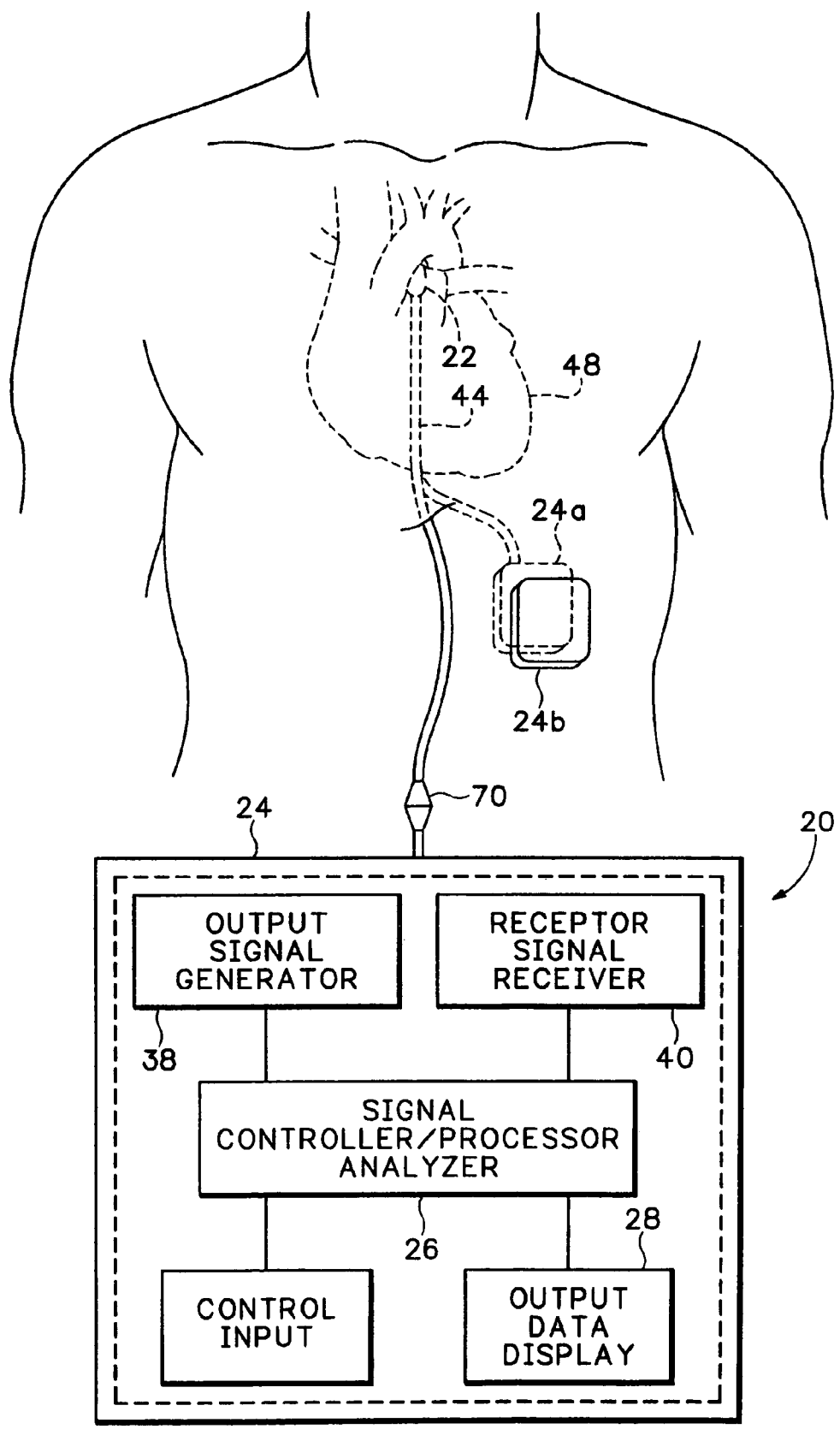
FIG. 1 is a frontal view of a person in whom an apparatus according to one embodiment of the invention is being used to evaluate the person's cardiopulmonary function, together with a block diagram of part of the apparatus.

Referring now to FIGS. 1-7 of the drawings which form a part of the disclosure herein, a blood condition monitor 20 includes an implantable sensor section 22 and an electronics portion, or control unit 24, which may include an electronic controller and processor package 26 and an associated output data display section 28. The sensor section 22 of the blood condition monitor 20 includes a sensor carrier 30 and associated non invasive sensors 32 and 34 used to quickly and conveniently determine the condition of a patient's blood without the need to withdraw blood samples from the patient.

Figure 2:
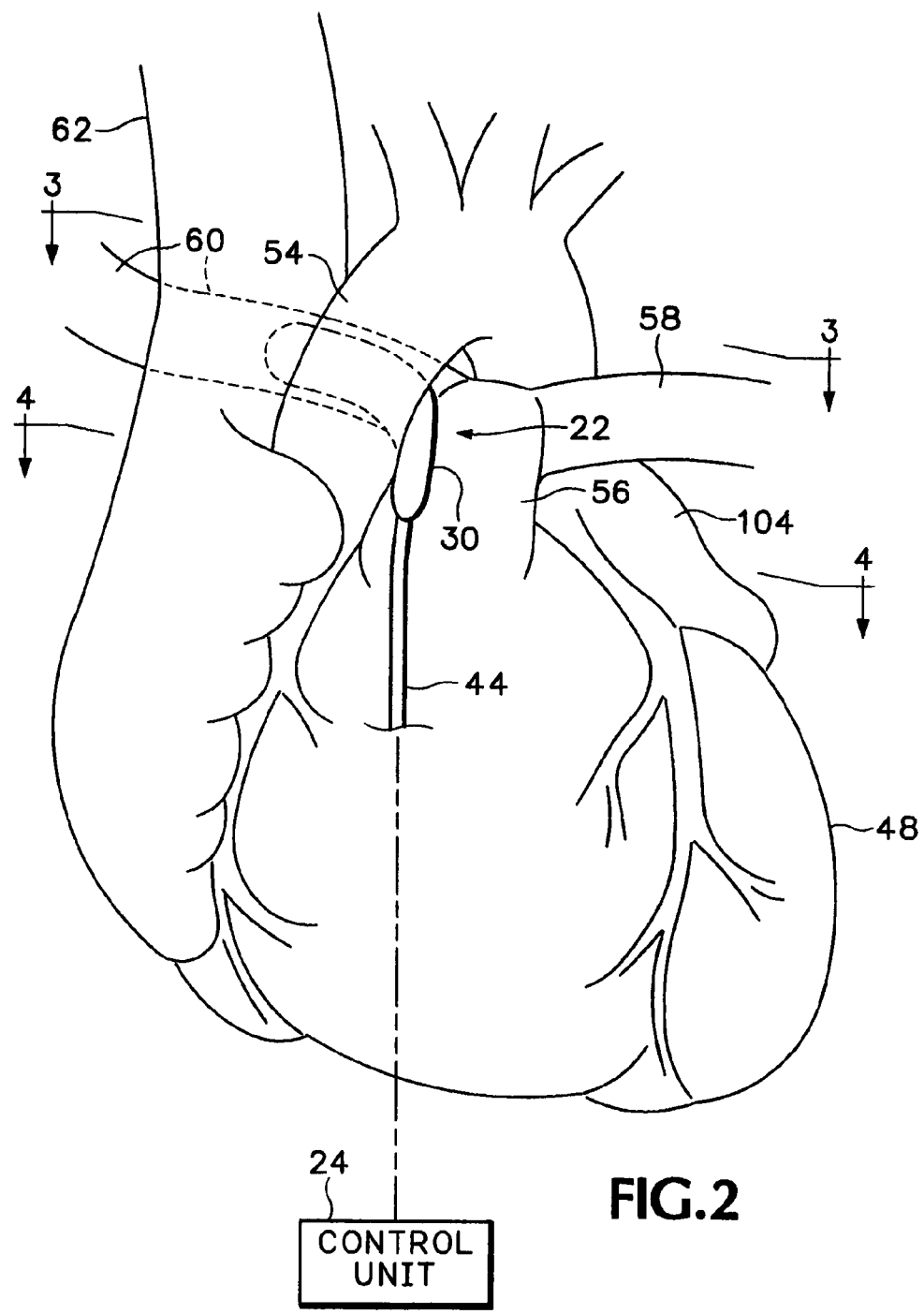
FIG. 2 is a view showing the anterior side of a human heart together with a sensor carrier in place according to the present invention, and also showing some of the major blood vessels that interconnect the heart with the lungs and other body parts.

The control unit 24 shown in simplified form in FIGS. 1-2 includes an electronic emitter signal generator portion 38, an electronic receptor signal receiver portion 40, and the output data display section 28. Preferably, the control unit 24 is provided as a self-contained unit incorporating suitable integrated circuit logic and data handling components to accept user instructions and provide for control of operation of the blood character monitor 20, and to provide signals to the output data display 28, which may include a suitable LCD array or other displays, to indicate the blood characteristics and constituent values determined by the device.

The sensor section 22, as shown in FIGS. 2-7, includes a sensor carrier 30, connected electrically to a suitable cable 44 that can be left extending out through a patient's abdominal or chest wall to the control unit 24 after the completion of thoracic surgery, as shown in FIG. 1. Alternatively, if a sensor carrier 30 is to be left in place for an extended time, a control unit 24a equipped to communicate percutaneously with an external unit 24b shown in simplified form, may be implanted in the patient, as shown broken line in FIG. 1. Thus, in one version of the apparatus disclosed herein, a sensor carrier 30 with a set of sensors 32, 34, etc., may be implanted in a patient, to be left in place for an extended period of time. In such a case the cable 44 including the sensor conductors may extend to a control and power package including a communication module (not shown) implanted within the patient. Known devices (not shown) depending, for example, on electromagnetic coupling and digital signal transmission, may be utilized in connection with such a communication module to monitor the patient's blood condition periodically.

Figure 3:
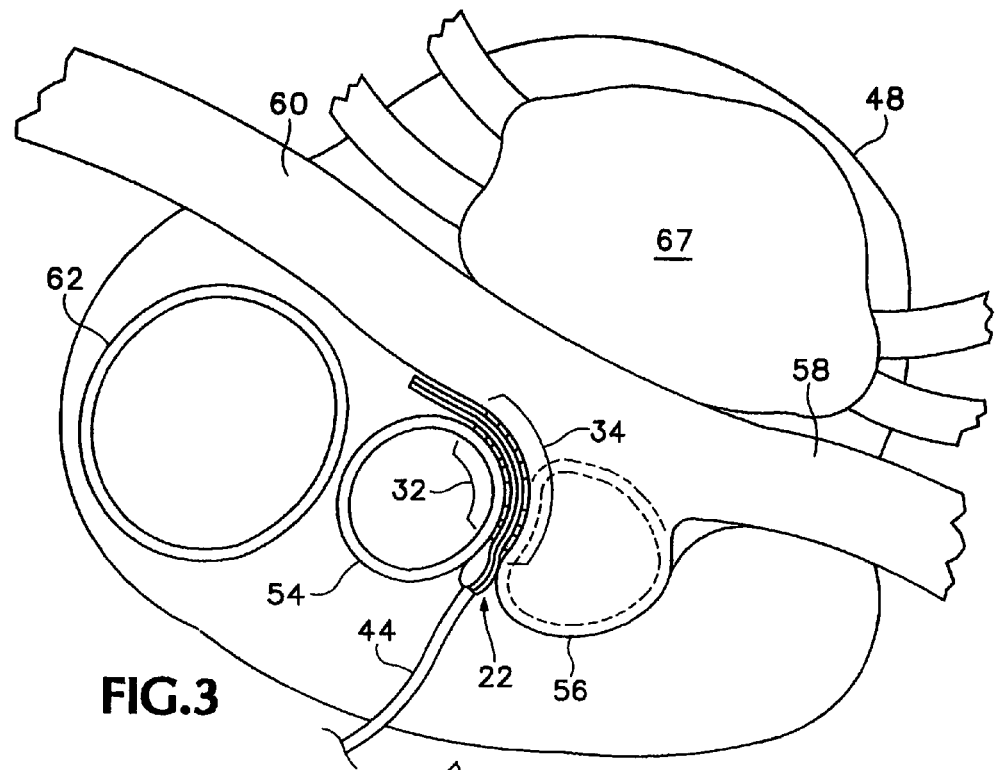
FIG. 3 is a simplified sectional view of the major blood vessels above the heart, taken along line 3-3 in FIG. 2, and showing the sensor carrier in place adjacent those blood vessels.
Figure 4:
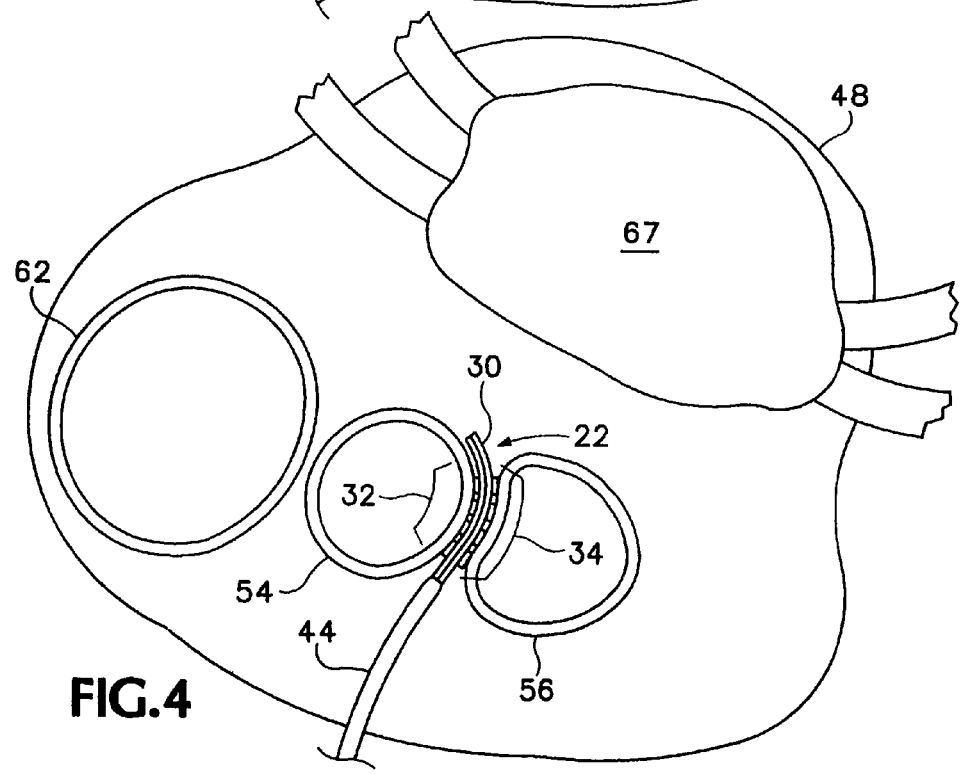
FIG. 4 is a simplified sectional view of the heart and major blood vessels shown in FIG. 2, taken along line 4-4, with the sensor carrier in place.

The sensor carrier 30 is preferably constructed of inert and suitably flexible elastomeric material such as a molded rubberlike thermoplastic material in the form of a ribbon-like strip, having a thickness 46 small enough to allow the sensor carrier 30 to be placed in the space that can be made available adjacent to the major thoracic blood-containing structures in which a characteristic of blood is to be sensed, for example, about 6 mm. At least a sensor 32, and preferably at least a pair of sensors 32 and 34 are located on the sensor carrier 30 in respective positions as shown in FIGS. 2-6. Thus, the sensor 32 is on a first face of the sensor carrier 30, mounted in the layer 47 of material while the sensor 34, if present, is located on the opposite, or second, face of the sensor carrier mounted in the layer 49, and the sensors 32, 34 are directed oppositely outward from the faces on which they are located. Each of the sensors 32, 34 is located adjacent and preferably in contact with a respective major blood vessel or a portion of the heart 48 when the sensor carrier 30 is located properly, as shown in FIGS. 2 and 3. While two sensors 32 and 34 may thus be located on opposite faces of the sensor carrier 30 they may both be on the same face of the sensor carrier 30, so as to sense two different characteristics of blood in one blood vessel.

For ease of collective reference, the term major thoracic blood-containing structures will be used to refer to any or all of the major veins, arteries, and portions of the heart adjacent to which the sensor carrier 30 or a variation thereof can be used, namely: the aorta, including the ascending aorta, the aortic arch, and the descending aorta, the main pulmonary artery and the right and left pulmonary arteries, the right and left carotid arteries, the right and left subclavian arteries, the inominate artery, the inferior vena cava, the superior vena cava, the pulmonary veins, the brachiocephalic vein, the azygous vein, and the left atrium and the right atrium of the heart.

Preferably, each sensor 32, 34 includes a respective emitter portion 50 or an array of such emitter portions 50, as will be explained presently, and a receptor portion 52 or an array of such receptor portions 52, which may be closely associated with each other or spaced slightly apart from each other, depending on the particular type of sensor utilized to determine a particular characteristic of the patient's blood.

The emitter 50 of a sensor 32 or 34 may include one or more electrically powered and controlled light-emitting components such as light-emitting diodes, designed to emit light in one or more selected wavelengths. Light in wavelengths outside the humanly visible spectrum, such as infrared and ultraviolet light, may be useful. Preferably, a sheet or layer 53 of flexible material substantially opaque to the light or other form of energy emitted by the emitters 50 is present in the sensor carrier 30 or 30', as shown best in FIG. 7, to prevent sensors in the opposite faces from interfering with each other. The sensor carrier 30 or 30', including the sensors 32, 34, etc., may be protected by a sterilizable layer 55 of flexible plastic or rubberlike material that is transparent to the type of light or other energy utilized by the sensors 32, 34, etc. The sensor carrier 30 or 31 may also be provided with a thin coating 59 of a hydrophilic material to facilitate its placement and removal.

The receptor 52 in each sensor 32, 34, etc., may include a suitable light-sensitive electronic component such as a photodiode or other opto-electric device capable of measuring an amount of received light in a selected wavelength range and producing an electrically detectable result such as a change in voltage or current. As shown in FIGS. 3-7, each receptor 52 should be properly located in the sensor 32 or 34 to be able to detect light that has been emitted from a respective emitter 50 and that has then passed through the wall of the intended blood vessel, through a portion of the blood contained within the blood vessel, and again through the wall of the blood vessel into the receptor 52. Thus, the receptor 52 may be closely alongside the corresponding emitter 50, or it may be separated from the emitter 50 along the blood vessel by some distance, or it may be located far enough from the emitter 50 to be located on an opposite side of the blood vessel whose blood is being examined, with a part of the sensor carrier 30 being wrapped partway around the blood vessel.

It is desirable to evaluate blood at or near the same time in each of the separate blood vessels where the sensors 32, 34, etc., are located, but some amount of time between measurements in the separate blood vessels is generally not critical in measuring the various components and characteristics of the blood, and measurements made within a minute or two can be considered to be substantially simultaneous. The closer together in time measurements are made of the blood in different blood vessels or parts of the heart, the more accurate the resulting evaluation of cardiac or cardiopulmonary function will be, but even measurements made an hour apart can be useful for comparisons.

Figure 9:
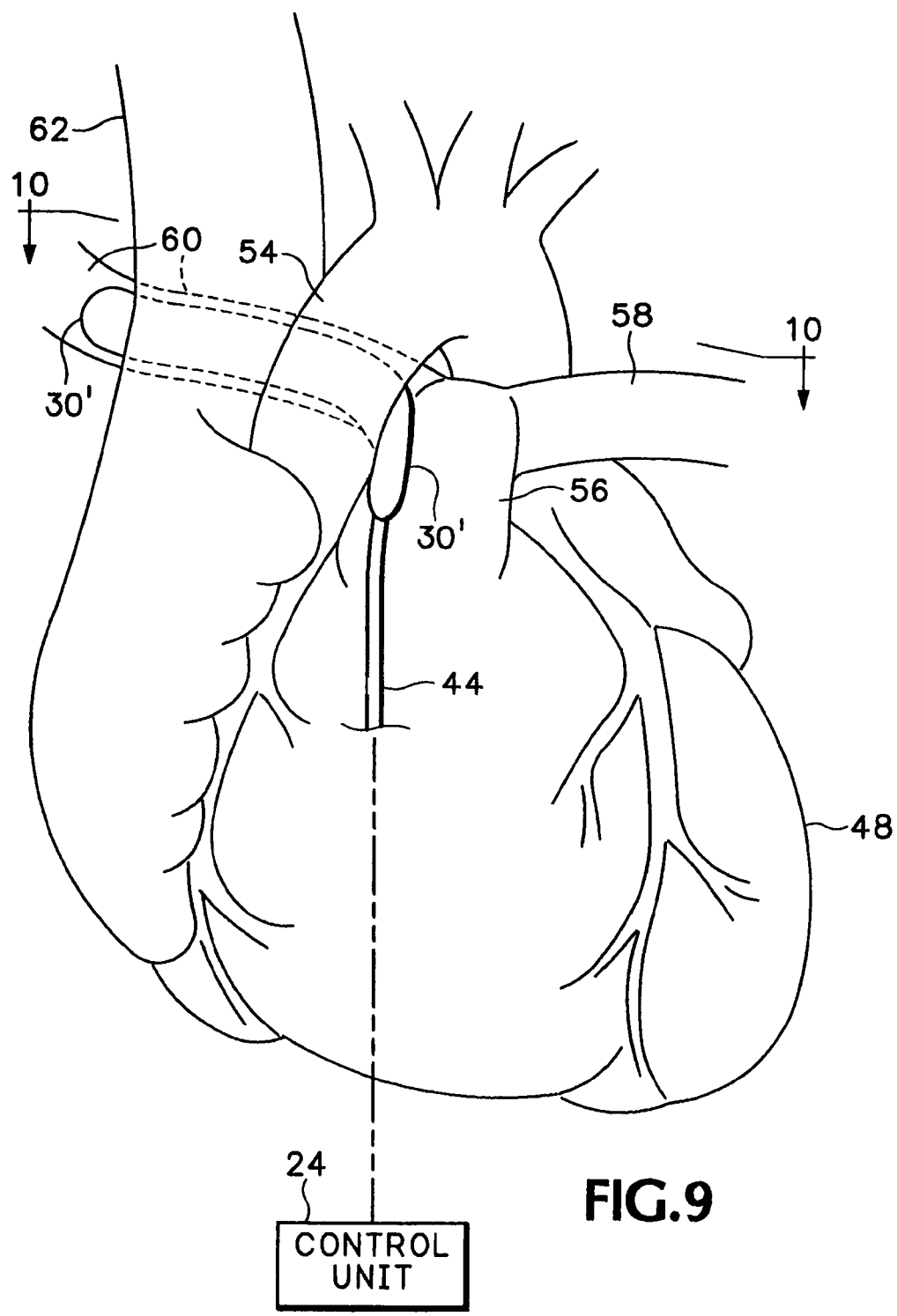
FIG. 9 is a view similar to FIG. 2, showing the sensor carrier shown in FIG. 8 in place adjacent a patient's heart.
Figure 9A:
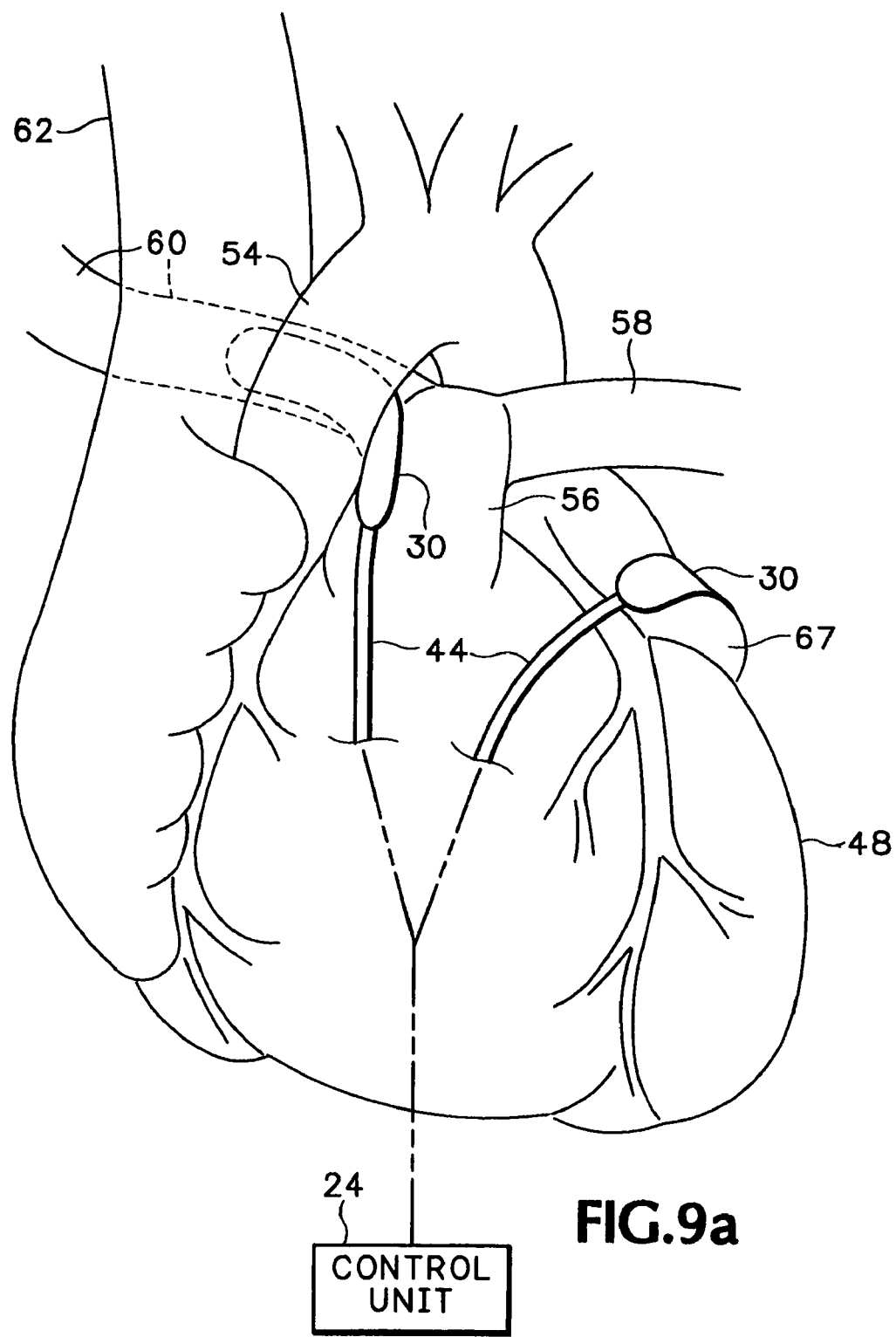
FIG. 9A is a view similar to FIG. 2, showing the use of a pair of separate sensor carriers adjacent to a patient's heart.

The sensor carrier 30 is most preferably installed between the aorta 54 and the main pulmonary artery 56, and extending along the right pulmonary artery in contact with both, in a space which must be created surgically, by dissecting connective tissue that ordinarily binds together several major blood vessels near their points of conjunction with the base of the heart 48. The sensor carrier 30 may instead lie alongside or extend partially around the aorta 54 or pulmonary artery 56 as shown in FIG. 9, or there may be two separate sensor carriers 30, as shown in FIG. 9A, with each carrier 30 located in contact with a separate major thoracic blood-containing structure. For example, one sensor carrier 30 may be located in contact with the aorta 54 while the other is located in contact with the left atrium 67.

Suitable tabs or ears 57 may be provided on the sensor carrier 30, as shown in FIG. 5, as convenient places to attach sutures to hold the sensor carrier 30 in place, although sutures may be deemed unnecessary in many cases. Suitable sutures may be fastened through the ears 57 to attach the sensor carrier to the adventitia of the aorta 54, the pulmonary artery 56, or another major blood vessel to retain the sensor carrier in a required position during surgery and for a subsequent period of time after which the sensor carrier 30 can be removed by pulling it out, breaking the sutures, without endangering the patient. It may also be desirable to keep the sensor carrier 30 in place for an extended time to facilitate long-term monitoring of the blood and to provide data useful for controlling a ventricular assist device, an artificial heart or a pacemaker.

As shown in FIGS. 2 and 3, the sensor 32 is located properly on the sensor carrier 30 to be able to evaluate a chosen characteristic of the blood in the patient's aorta 54, while the sensor 34 is located on the sensor carrier 30 in an appropriate position to be able to evaluate a characteristic of the patient's blood in the main pulmonary artery 56 substantially simultaneously. The sensor 34 might, instead, be located in a position better adapted to evaluate blood in one of the left and right branches 58, 60 of the pulmonary artery, if desired.

Figure 10:
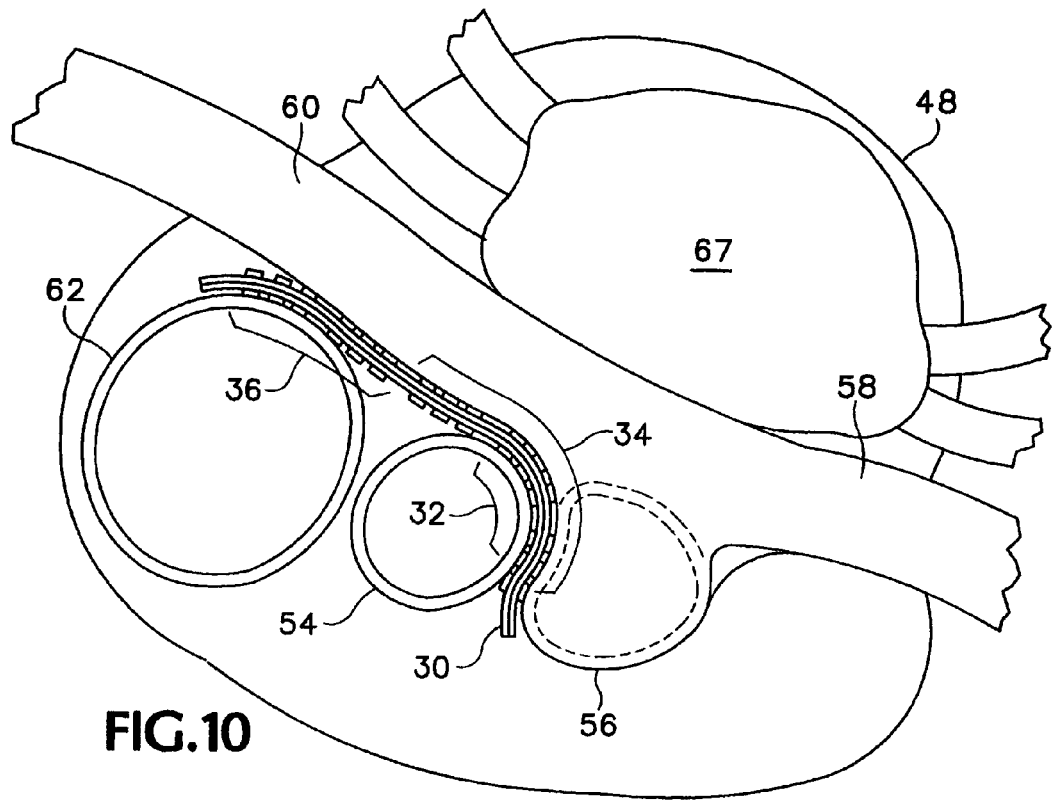
FIG. 10 is a view similar to FIG. 3, taken along line 10-10 of FIG. 9, showing the sensor carrier shown in FIG. 8 in place adjacent a patient's heart.

A third sensor 36 may also be provided in an alternative sensor carrier 30', as shown in FIG. 8. The third sensor 36 is located on the same face of the carrier 30' as the sensor 34 so as to evaluate a chosen characteristic of the blood in the patient's superior vena cava 62, as shown in FIGS. 9 and 10, when the sensor carrier 30' is properly located with respect to the patient's heart 48. Placement of the sensor carrier 30' also requires that a space posterior and adjacent to the superior vena cava be created by cutting through or into a portion of the associated connective tissue between the superior vena cava and the right pulmonary artery. Similarly, using an appropriate sensor carrier, sensors may be placed adjacent the inferior vena cava.

Figure 11:
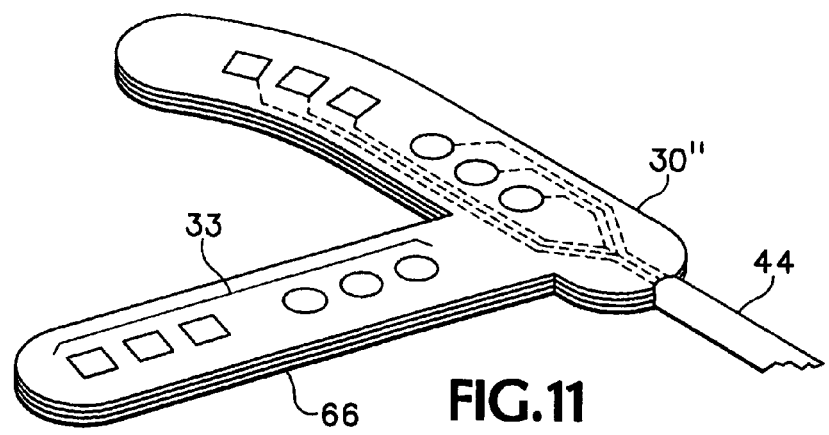
FIG. 11 is a perspective view, similar to FIG. 5, showing a sensor carrier that is another embodiment of the apparatus of the present invention.
Figure 12:
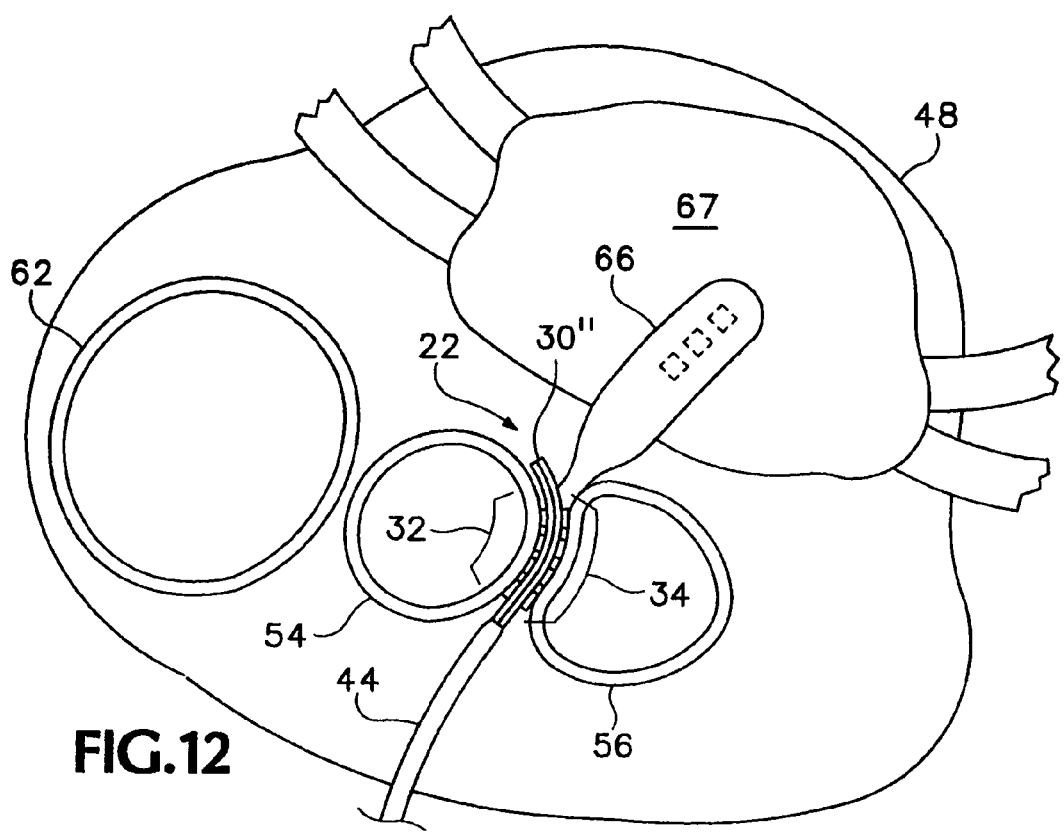
FIG. 12 is a view similar to FIG. 4, showing the sensor carrier shown in FIG. 11 in place adjacent a patient's heart.

As shown in FIGS. 11 and 12, a sensor carrier 30" may include a ribbon-like branch portion 66 carrying a sensor 33 to sense selected characteristics of blood in the left atrium instead of, or in addition to, sensing the blood in the aorta 54. As shown in FIG. 12, the branch 66 of the sensor carrier 30" is placed on the exterior of the dome 67 of the left atrium of the heart 48 in position to emit energy into and receive energy from blood in the left atrium through its dome. Alternatively, the branch 68 can be placed effectively against the pulmonary veins near their points of entry into the left atrium. An appropriately shaped sensor carrier (not shown) can also be used in a similar manner to place such sensors adjacent to the right atrium or another structure of the heart.

Suitable electrical conductors such as small, flexible, insulated wires or pairs of wires 64, 68 (FIGS. 5, 8) extend from each sensor 32, 34 or 36 along the body of the sensor carrier 30 through the cable 44. It will be understood that there may be a different number of such conductors, depending on the structures of the particular sensors 32, 34, and the wires 64, 68 are merely representative of one possibility. The wires 64, 68 of the cable 44 are connected electrically to the control unit 24 outside the patient's body by suitable connectors such as, for example, a plug and socket combination 70 (FIG. 1). The conductors 64 may thus carry control signals and power from the control unit 24 to the emitter 50 to cause it to transmit energy in a suitable form, such as a pulse of light, toward an adjacent blood-containing structure. The conductors 68 may carry electricity between the control unit 24 and the receptor 52 to energize the receptor 52 and enable it to provide a signal to the signal receiver portion 40 of the monitor 20, in response to detection of the relevant form of energy.

Preferably, the emitters 50 can simultaneously or sequentially emit quantities of light or another suitable form of energy in two or more discrete wavelengths or frequencies. The receptors 52, in turn, are sensitive to the same form of energy and function to receive portions of the energy transmitted by the emitters 50 and not absorbed in the blood and surrounding tissues. The receptors 52 thus receive some of the emitted energy that has been conducted or reflected by the blood and blood vessel walls in wavelengths or frequencies including those radiated by the emitter. It may also be necessary or desirable for a receptor 52 to be sensitive to light of a different wavelength in order to detect, for example, fluorescence of a substance added to the patient's blood as an identifier, in response to energy emitted from the appropriate emitter 50.

Simultaneous or sequential emission and reception of and evaluation of light of three different wavelengths can reduce or eliminate ambiguity in interpreting the condition of blood being evaluated by a particular one of the sensors 32, 34, 36. A particular combination of levels of transmission or reflectance of light of different wavelengths by the blood can be interpreted reliably as an indication of a certain level of concentration of a particular blood constituent, or of a particular value of, a blood characteristic of interest.

It is particularly desirable to determine the oxygen saturation level of the blood, that is, the percentage of saturation by oxygen of the hemoglobin component of the blood, substantially simultaneously both in a blood vessel such as the aorta 54, where freshly oxygenated blood is present, and in a blood vessel, such as the pulmonary artery 56, where mixed venous blood, whose oxygen content is naturally lower than that of the blood in the aorta, is present. By determining and comparing the oxygen saturation level of the freshly oxygenated blood, as in the aorta 54, and of the mixed venous blood, as in the pulmonary artery 56, the patient's cardiopulmonary performance can be determined in accordance with the Fick principle to calculate the patient's cardiac output and cardiac index.

Cardiac output or cardiac index can be used to monitor whether a patient is generally dealing successfully with the stress of surgery.

By using the information made available by sensing characteristics of blood in one of the major thoracic blood-containing structures it is also possible to diagnose, more specifically than has previously been possible, an abnormal shunt of blood, indicating an anatomic or physiological deficiency within the heart or lungs. For example, the percentage of oxygen saturation of blood in the pulmonary artery or right atrium, left atrium, or aorta can be compared with the percentage of oxygen saturation of blood in other chambers of the heart to detect an abnormal shunt of blood from one chamber to another. As a further example, if the blood in the right atrium has 62 percent oxygen saturation and the blood in the aorta has 100 percent oxygen saturation, but the blood in the pulmonary artery has 85 percent oxygen saturation, there is apparently a shunt from the left side to the right side of the heart. Similarly, a shunt in the lungs could be indicated by oxygen saturation less than 100 percent in blood present in the left atrium. Such information can also indicate whether surgery has successfully repaired blood shunt conditions within a patient.

Light absorption, transmission, and reflectance values of blood are known for light in various wavelengths directed into blood of various oxygen saturation levels. These values can be stored as data in the microprocessor 26 in the blood monitor control unit 24. Signals from the receptors 52 of the sensors 32, 34 located adjacent to the aorta and the pulmonary artery can be interpreted by the microprocessor 26 to periodically evaluate the percentage of oxygen saturation present in the aortic or mixed venous blood.

Secondarily, the level of hemoglobin in the blood or the percentage of the blood that is made up of red blood cells, both of which affect the ability of the blood to deliver oxygen to the cells, may similarly be evaluated by the use of appropriate sensors 32, 34 transmitting light in appropriate wavelengths into the blood contained in a major blood vessel such as the aorta or the pulmonary artery and using the receptors 52 to measure the light that is returned from the aorta or pulmonary artery.

Specific non-invasive sensors 32, 34 and 36, which may function similarly, can also be used in the locations shown in FIGS. 2, 3, 4, 9, 9A and 10 to evaluate the hemoglobin content, hematocrit, potassium content, lactate content, glucose content, or pH of blood in a major thoracic blood-containing structure such as the pulmonary artery, the aorta or the superior vena cava by utilizing emissions of the appropriate type of energy and subsequent detection of quantities of that energy that has passed through or been reflected by blood contained in the particular blood containing structure.

It should be understood that while the sensors 32, 34, 36 have been described as operating by measuring transmission of light, such light need not be of frequencies in the spectrum visible to humans. Additionally, in order to measure certain characteristics or the amounts of certain components of the blood it may be desirable to add to the blood a chemical identifying agent that can become attached chemically to certain blood components. Such an identifier can cause fluorescence varied in intensity in relation to the amount of such a blood component, in response to light emitted in a particular wavelength by a sensor.

Also, various sensors 32, 34 and 36 may be utilized which emit and receive and evaluate the transmission of ultrasound through blood contained in the respective major thoracic blood containing structure, or which evaluate optical coherence resonance of the blood, or which transmit and receive and evaluate the interaction with the blood of energy other than visible light, such as infrared light, ultraviolet light, radio frequency energy, for which the characteristics of absorption or transmission through blood and blood vessel walls or a measurable harmless effect on the blood can be utilized to analyze the blood characteristic of concern.

Figure 13:
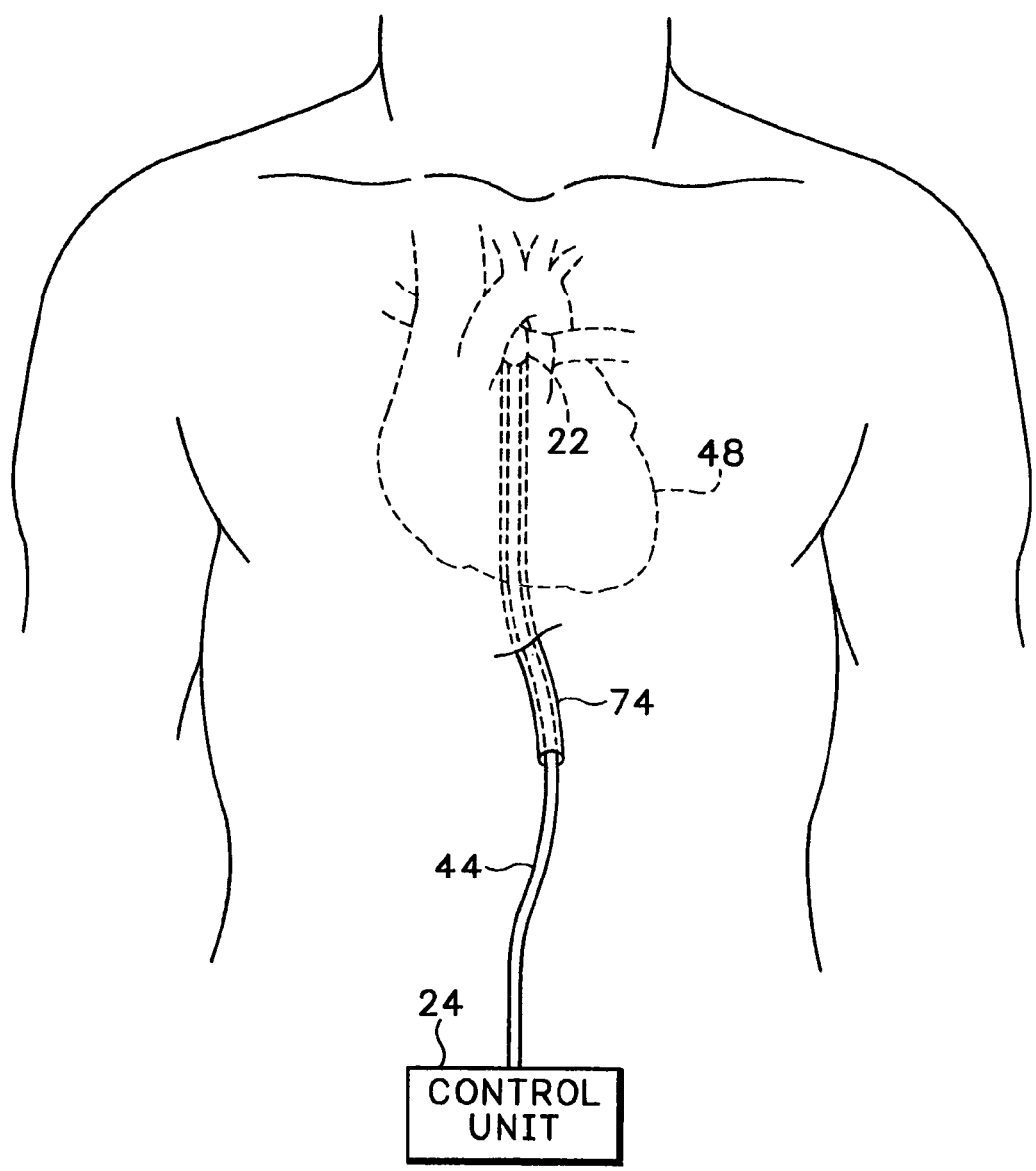
FIG. 13 is a view of a sensor carrier protected by a flexible tube attached to a support member and extending outward from a surgical opening.

For the use of sensors 32, 34 and 36 that may be considered too expensive for disposal after a single period of use or that cannot be sterilized without suffering damage, the sensor carrier 30 or 30' may be enclosed in a flexible sensor-protective sleeve 74 as shown in FIG. 13.

Figures 14, 15, 16:
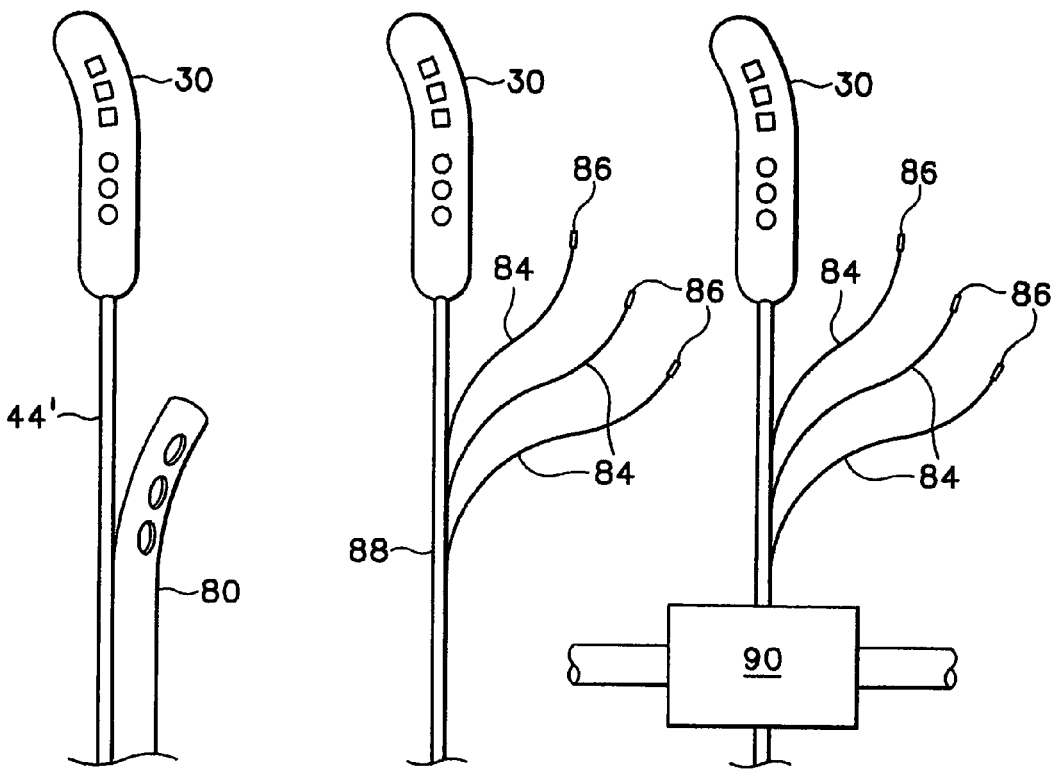
FIG. 14 is a view of a sensor carrier according to the present invention with a chest drain tube supporting a sensor conductor cable.
FIG. 15 is a view of a sensor carrier according to the present invention together with a sensor conductor cable with which cardiac pacing leads and electrodes are associated.
FIG. 16 is a view of a sensor carrier and sensor conductor cable according to the present invention together with a ventricular assist device and a set of cardiac pacing leads.

When it is intended to leave the sensor carrier in place for a time after completion of surgery, the sensor carrier may be interconnected through a cable 44' that may be attached to a support member such as a chest drain tube, as shown in FIG. 14.

In some patients cardiac pacing leads 84 including suitable electrodes 86 as shown in FIG. 15 may be connected to the patient's heart 48. In some cases pacing is needed only temporarily, while in others implantation of pacing leads is intended to be permanent. The pacing leads 84 are preferably included in a cable 88 interconnected with the sensor carrier 30 or 30' of an implantable sensor section 22 as previously described herein, and the sensor carrier 30 or 30' can remain in place adjacent the patient's heart and associated major blood vessels so long as the pacing leads 84 are in place.

Similarly, it may be desirable in certain patients to have the sensor carrier 30 or 30' and sensors 32, 34, etc., disclosed herein remain substantially permanently implanted. In such a situation, the electrical conductors for the sensors 32, 34, etc., disclosed herein may be included in a cable 88 together with pacing leads 84 as shown in FIG. 15. An implantable communication and power device as mentioned above may be connected with the cable 88 and may be included with the power and control devices for a pacemaker, as a single implanted package (not shown) including the ability to communicate percutaneously with a related external unit.

As a similar and somewhat related application, the sensor carrier 30 and sensors 32, 34, etc., may be implanted in a patient along with a ventricular assist device 90, as shown in FIG. 16, so that sensor-derived information, particularly cardiac output information, available as a result of the use of the sensors 32, 34, etc., may be utilized in connection with operation and control of the ventricular assist device 90.

Figure 17:
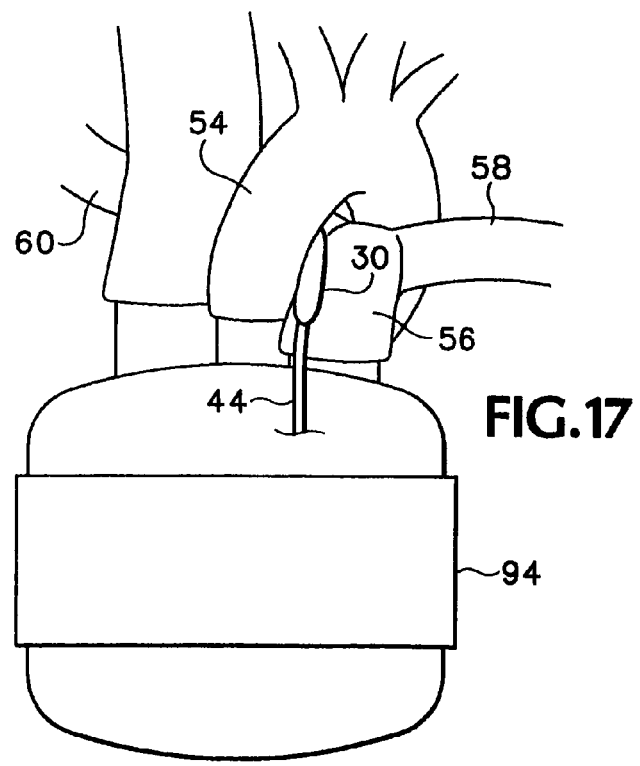
FIG. 17 is a view of an implanted artificial heart showing the placement of a sensor carrier according to the present invention adjacent the patient's aorta and pulmonary artery.

Referring now to FIG. 17, in the case of an implanted artificial heart 94, the patient's blood condition and the performance of the artificial heart 94 may be monitored by use of the sensor carrier 30 and sensors 32, 34, etc., disclosed herein, since the artificial heart 94 will be connected to the major blood vessels of the patient's own circulatory system. The control unit (not shown) for the sensor 32, 34, etc., may also be associated with the controller for the artificial heart.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. Apparatus for measuring a selected characteristic of a patient's blood, comprising:
   (a) a sensor carrier including a flexible sheet-like member having a pair of opposite faces;
   (b) first and second electronic sensors mounted on said sensor carrier, said first sensor being directed outwardly from a first one of said pair of opposite faces and said second sensor being directed outwardly from the other one of said pair of opposite faces, each of said first and second sensors having a respective receptor capable of providing a receptor output signal representative of a level of a selected characteristic of blood within an adjacent blood-containing structure, said sensor carrier and said first and second sensors collectively being small enough to be placed within said patient's body cavity and proximate said patient's heart, permitting substantially simultaneous observation of blood in a first blood-containing structure by said first sensor and of blood in a second blood-containing structure by said second sensor without mechanical penetration of either of said blood-containing structures by either of said first and second sensors.

2. The apparatus of claim 1, wherein said sensor carrier has a coating of a hydrophilic material.

3. The apparatus of claim 1, wherein each of said first and second sensors includes an emitter adapted to transmit energy into blood within a respective one of said first and second blood-containing structures and a receptor sensitive to energy from said emitter that has passed through said blood inside respective one of said first and second blood-containing structures.

4. The apparatus of claim 3 wherein said emitter of one of said sensors is a radio frequency transmitter and said receptor of said one of said sensors is a radio frequency receiver.

5. The apparatus of claim 3 wherein each of said emitters is an electrically driven light emitter.

6. The apparatus of claim 3 wherein one of said sensors includes a plurality of said receptors, each of said receptors measuring reception of light in a different respective wavelength and providing a respective signal representative thereof.

7. The apparatus of claim 1, wherein at least one of said sensors separately measures reception of light in each of a plurality of different wavelengths and provides a respective signal representative of reception of light in each of said different wavelengths.

8. The apparatus of claim 1, wherein one of said sensors includes an ultrasound transducer.

9. The apparatus of claim 1, wherein said sensor carrier includes a suture tab.

10. The apparatus of claim 1, including a sterile protective sleeve surrounding said sensor carrier.

11. The apparatus of claim 1, wherein said sensor carrier is of a flexible material.

12. The apparatus of claim 1 wherein said sensor carrier includes an emission-opaque central layer located between said opposite faces and separating said first and second sensors from each other.

13. The apparatus of claim 1 including a cable including a plurality of cardiac pacing leads, and wherein said sensors are connected to a control unit through said cable.

14. The apparatus of claim 1 including a cable associated with a ventricular assist device, and wherein said sensors are connected electrically with a control unit through conductors included in said cable.

15. The apparatus of claim 14 wherein said sensors are connected electrically with a control unit of said ventricular assist device, thereby providing to said ventricular assist device a signal representative of a patient's cardiac function.

16. The apparatus of claim 14 wherein said sensors are connected electrically with a control unit of a said ventricular assist device, thereby providing to said ventricular assist device a signal representative of a patient's cardiopulmonary function.

17. The apparatus of claim 1 including a cable associated with an artificial heart, and wherein said sensors are connected electrically with a control unit through conductors included in said cable.

18. The apparatus of claim 17 wherein said control unit is connected electrically with a controller of said artificial heart, thereby providing to said control unit of said artificial heart a signal representative of how effectively said artificial heart is functioning.

19. The apparatus of claim 1, including a cable associated with a pacemaker, and wherein said sensors are connected electrically with a control unit through said cable.

20. The apparatus of claim 1, wherein said control unit is connected electrically with a control unit of a pacemaker thereby providing to said pacemaker a signal representative of a patient's cardiac function.

21. The apparatus of claim 1, wherein said sensors are connected electrically with a control unit through a cable attached to a mediastinal chest drain tube.

22. The apparatus of claim 1, further including a second sensor carrier and a respective sensor mounted thereon capable of providing a receptor output signal representative of a level of a respective selected characteristic of blood in an adjacent blood-containing structure.

23. The apparatus of claim 1, wherein each of said sensors is connected functionally with an implantable control unit equipped to communicate wirelessly and percutaneously with an external unit.

24. The apparatus of claim 1 wherein said selected characteristic of blood is glucose content of said blood.

25. The apparatus of claim 1 wherein said selected characteristic of blood is potassium content of said blood.

26. The apparatus of claim 1 wherein said selected characteristic of blood is lactate content of said blood.

27. A method of at least partially evaluating a selected aspect of a patient's metabolic function, comprising:
measuring separately at least one characteristic selected from the group consisting of glucose content, potassium content, and lactate content of blood present in each of at least two selected major thoracic blood-containing structures by using at least two electronic sensors, located within said patient's thoracic cavity but outside all of said selected major thoracic blood-containing structures, to observe said blood through a respective wall of each of said selected major thoracic blood-containing structures without inserting a sensor into any of said selected major thoracic blood-containing structures, and comparing respective values of said at least one characteristic as measured in each of said at least two selected major thoracic blood-containing structures by said at least one electronic sensor, by performing the steps of:
(a) providing a sensor carrier having at least two electronic sensors mounted thereon;
(b) surgically creating a space for said sensor carrier between two of said at least two selected major thoracic blood-containing structures;
(c) placing said sensor carrier into said space;
(d) directing a first quantity of energy toward a first of said selected major thoracic blood-containing structures from an emitter portion of said first one of said at least two electronic sensors and receiving a portion of said first quantity of energy in a receptor portion of said first one of said at least two electronic sensors located closely adjacent said first of said selected major thoracic blood-containing structures, and forming an electrical signal from said receptor portion of said first one of said at least two electronic sensors representative of said portion of said energy received thereby;
(e) directing a second quantity of energy toward a second of said selected major thoracic blood-containing structures from an emitter portion of a second one of said at least two electronic sensors and receiving a portion of said second quantity of energy in a receptor portion of said second one of said at least two electronic sensors located closely adjacent said second of said selected major thoracic blood-containing structures, and forming an electrical signal from said receptor portion of said second one of said at least two electronic sensors representative of said portion of said energy received thereby;
(f) from said electrical signal from said receptor portion of said first one of said at least two electronic sensors determining a measurement of said at least one selected characteristic of said blood in said first of said selected major thoracic blood-containing structures; and
(g) from said electrical signal from said receptor portion of said second one of said at least two electronic sensors determining a measurement of said at least one selected characteristic of said blood in said second of said selected major thoracic blood-containing structures.

28. The method of claim 27, wherein one of said at least two selected major thoracic blood-containing structures is said patient's aorta.

29. The method of claim 27, wherein one of said at least two selected major thoracic blood-containing structures is said patient's main pulmonary artery.

30. The method of claim 27, wherein one of said at least two selected major thoracic blood-containing structures is said patient's right pulmonary artery.

31. The method of claim 27, wherein one of said at least two selected major thoracic blood-containing structures is said patient's left pulmonary artery.

32. The method of claim 27, wherein one of said at least two selected major thoracic blood-containing structures is said patient's left atrium.

33. The method of claim 27, wherein one of said at least two selected major thoracic blood-containing structures is said patient's inferior vena cava.

34. The method of claim 27, wherein one of said at least two selected major thoracic blood-containing structures is said patient's superior vena cava.

35. The method of claim 27, wherein one of said at least two selected major thoracic blood-containing structures is of patient's right atrium.

36. The method of claim 27, wherein one of said at least two selected major thoracic blood-containing structures is one of said patient's pulmonary veins.

37. The method of claim 27, wherein one of said at least two selected major thoracic blood-containing structures is said patient's innominate artery.

38. The method of claim 27, wherein one of said at least two selected major thoracic blood-containing structures is one of said patient's carotid arteries.

39. The method of claim 27, wherein one of said at least two selected major thoracic blood-containing structures is one of said patient's subclavian arteries.

40. The method of claim 27, wherein said selected characteristic of blood is glucose content of said blood.

41. The method of claim 27, wherein said selected characteristic of blood is potassium content of said blood.

42. The method of either claim 40 or claim 41, including measuring lactate content as an additional selected characteristic of said blood.

43. The method of claim 27, wherein said selected characteristic of blood is lactate content of said blood.

44. The method of any of claims 40-43, including measuring the degree of saturation by oxygen of hemoglobin as an additional selected characteristic of said blood.

45. The method of any of claims 40-43, including measuring hemoglobin content as an additional selected characteristic of said blood.

46. The method of any of claims 40-43, including measuring hematocrit as an additional selected characteristic of said blood.

47. The method of any of claims 40-43, including measuring pH as an additional selected characteristic of said blood.

48. The method of either claim 41 or claim 43, including measuring glucose content as an additional selected characteristic of said blood.

49. The method of either claim 40 or claim 43, including measuring potassium content as an additional selected characteristic of said blood.

50. The method of claim 27, wherein said selected aspect of a patient's metabolic function is cardiac function.

51. The method of claim 27, wherein said selected aspect of a patient's metabolic function is cardiovascular function.

52. The method of claim 27, wherein said selected aspect of a patient's metabolic function is cardiopulmonary function.

53. The method of claim 27, wherein said selected aspect of a patient's metabolic function is pulmonary function.

54. The method of claim 27, wherein said selected aspect of a patient's metabolism is glucose metabolism.

55. The method of claim 27, wherein said selected aspect of a patient's metabolic function is biochemical metabolic function.

56. The method of claim 27, the step of providing said sensor carrier with said first one of said electronic sensors mounted on a first side thereof and said second one of said sensors mounted on an opposite second side thereof.

57. The method of claim 27, providing a third one of said at least one electronic sensor on said sensor carrier and placing said third one adjacent a selected third major thoracic blood-containing structure of said patient and measuring an amount of a selected blood constituent present in blood in said third major thoracic blood-containing structure by evaluating transmission and reception of a selected form of energy by said third one through a wall of said third major thoracic blood-containing structure.

58. The method of claim 27, the steps of leaving said sensor carrier in place for an extended time after first measuring said at least one selected characteristic of said blood, and periodically again measuring said at least one selected characteristic of said blood during said extended time.

59. The method of claim 27, said first and second ones of said at least one electronic sensor measure said at least one selected characteristic of said blood by measuring transmission of light through said blood.

60. The method of claim 59, including the steps of separately measuring transmission through said blood of light having each of a plurality of different wavelengths.

61. The method of claim 27, directing said quantities of energy from said first and second ones of said at least one electric sensor substantially contemporaneously toward said first and second of said selected major thoracic blood-containing structures.

62. The method of claim 27, said space is between said patient's aorta and right pulmonary artery, including the additional step of surgically forming a further space adjacent said patient's inferior vena cava and placing a part of said sensor carrier carrying a third sensor into said further space.

63. The method of claim 27 including the step of providing at least one additional said electronic sensor on a second sensor carrier and placing said second sensor carrier adjacent a respective one of said at least two selected major thoracic blood-containing structures.

64. The method of claim 27 including measuring separately at least two selected characteristics of blood present in at least one of said at least two selected major thoracic blood-containing structures by using said at least one electronic sensor.

65. The method of claim 27 including measuring said selected characteristic of blood substantially simultaneously in each of said at least two selected major blood-containing structures.

\* \* \* \* \*

UNITED STATES PATENT AND TRADEMARK OFFICE
CERTIFICATE OF CORRECTION

PATENT NO. : 8,078,249 B2
APPLICATION NO. : 11/367469
DATED : December 13, 2011
INVENTOR(S) : Anthony P. Furnary It is certified that error appears in the above-identified patent and that said Letters Patent is hereby corrected as shown below:

Column 14, claim 56, line 1: insert --including-- before "the step...";

Column 14, claim 57, line 5: insert --including-- before "providing...";

Column 14, claim 58, line 14: insert --including-- before "the steps...";

Column 14, claim 59, line 19: insert --wherein-- before "said first...";

Column 14, claim 61, line 26: insert --Including-- before "directing said...";

Column 14, claim 62, line 31: insert --wherein-- before "said space is between...";

Signed and Sealed this
Seventeenth Day of April, 2012

David J. Kappos
*Director of the United States Patent and Trademark Office*